US012690872B2

(12) United States Patent
Mattes et al.

(10) Patent No.: US 12,690,872 B2
(45) Date of Patent: Jul. 28, 2026

(54) MEDICAL SLIDING SHAFT INSTRUMENT

(71) Applicant: Aesculap AG, Tuttlingen (DE)

(72) Inventors: Richard Mattes, Duerbheim (DE);
Thomas Pleil, Bad Duerrheim (DE)

(73) Assignee: Aesculap AG, Tuttlingen (DE)

( * ) Notice: Subject to any disclaimer, the term of this
patent is extended or adjusted under 35
U.S.C. 154(b) by 328 days.

(21) Appl. No.: 17/737,312

(22) Filed: May 5, 2022

(65) Prior Publication Data

US 2022/0257255 A1     Aug. 18, 2022

Related U.S. Application Data

(63) Continuation of application No.
PCT/EP2020/081251, filed on Nov. 6, 2020.

(30) Foreign Application Priority Data

Nov. 8, 2019     (DE) ..................... 10 2019 130 223.4

(51) Int. Cl.
A61B 17/128 (2006.01)
A61B 17/122 (2006.01)

(52) U.S. Cl.
CPC ........ A61B 17/128 (2013.01); A61B 17/1227
(2013.01)

(58) Field of Classification Search
CPC .......... A61B 2017/0488; A61B 17/128; A61B
17/1285; A61B 2017/2912;
(Continued)

(56) References Cited

U.S. PATENT DOCUMENTS 5,611,813 A * 3/1997 Lichtman ........... A61B 18/1445
606/174
5,989,257 A 11/1999 Tidwell et al.
(Continued)

FOREIGN PATENT DOCUMENTS

CN     108135603 A     6/2018
DE     29800876 U1     3/1998
(Continued)

OTHER PUBLICATIONS

Search Report received in International Application No. PCT/
EP2020/081251 dated Jan. 12, 2021, with translation, 5 pages.
(Continued)

*Primary Examiner* — Kathleen S Holwerda
*Assistant Examiner* — James R McGinnity
(74) *Attorney, Agent, or Firm* — Christopher A. Rothe;
CM Law

(57)     ABSTRACT

A medical sliding shaft instrument includes a tool element
carrier, a tubular sliding shaft surrounding the tool element
carrier and defining a sliding direction, and an actuating
device for moving the sliding shaft relative to the tool
element carrier in the distal direction. At least one tool
element is arranged or movably mounted on the distal end of
the tool element carrier. The at least one tool element is
arranged or formed so as to cooperate with a distal end
region of the sliding shaft in such a way that the at least one
tool element is moved as a result of a movement of the
sliding shaft in the distal direction. The sliding shaft instru-
ment further comprises a locking device for blocking a
movement of the sliding shaft relative to the tool element
carrier in at least one advancing position.

20 Claims, 10 Drawing Sheets

Figure 1:
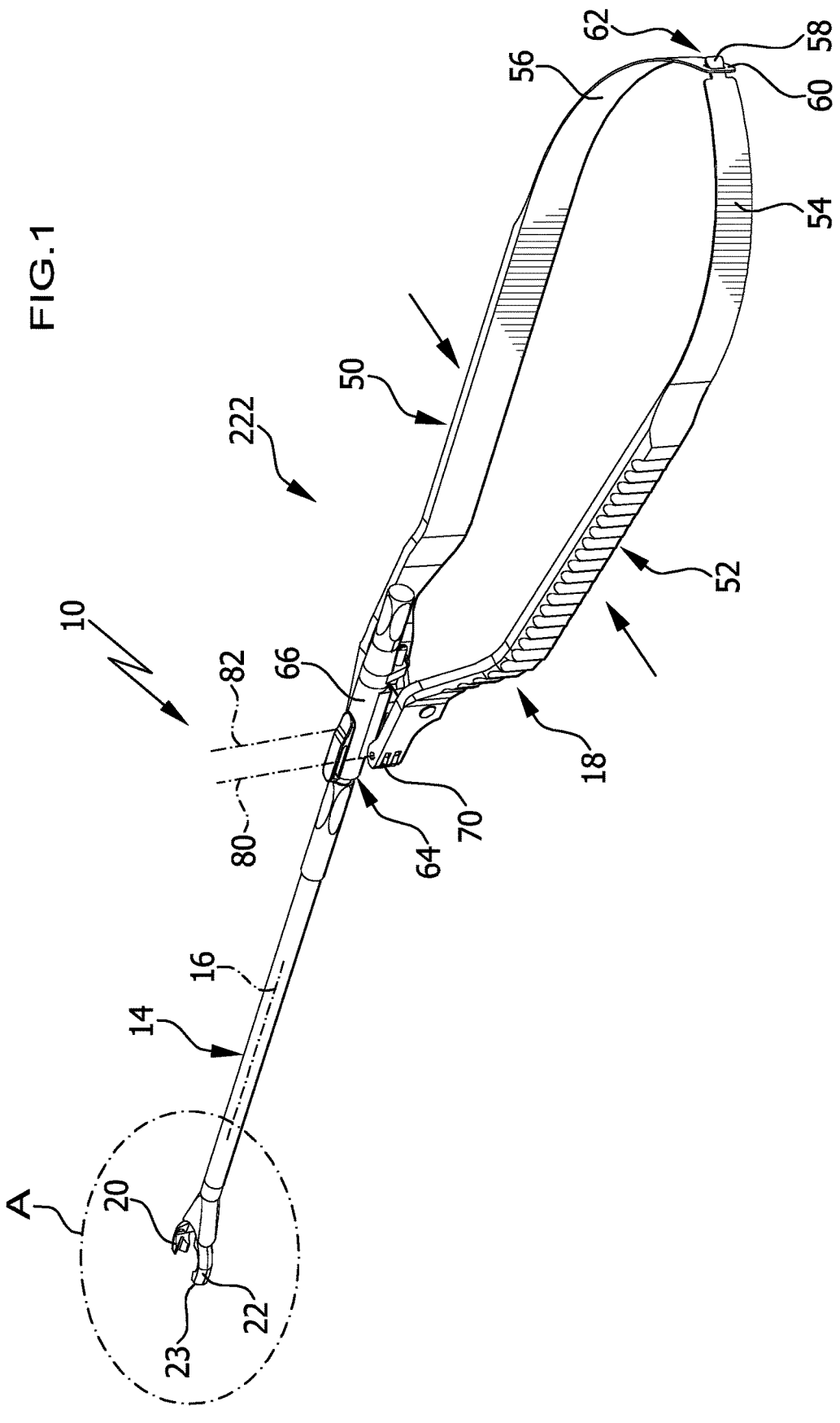

(58) Field of Classification Search
CPC .... A61B 2017/2913; A61B 2017/2915; A61B
2017/2916; A61B 2017/2917; A61B
2017/2919; A61B 2017/292; A61B
2017/2922; A61B 2017/2923
See application file for complete search history.

(56) References Cited

U.S. PATENT DOCUMENTS

| | | | |
|---|---|---|---|
| 9,387,003 B2 | 7/2016 | Kaercher et al. | |
| 2002/0013570 A1 | 1/2002 | Ruegg et al. | |
| 2003/0191478 A1 | 10/2003 | Kortenbach et al. | |
| 2008/0154299 A1 | 6/2008 | Livneh | |
| 2010/0318104 A1* | 12/2010 | Lazic | A61B 17/2812 |
| | | | 606/142 |
| 2011/0022062 A1* | 1/2011 | Hegemann | A61B 17/1227 |
| | | | 606/142 |
| 2012/0271347 A1 | 10/2012 | Kaercher et al. | |
| 2013/0184726 A1* | 7/2013 | Weisshaupt | A61B 17/1227 |
| | | | 606/158 |

| | | | |
|---|---|---|---|
| 2016/0331369 A9 | 11/2016 | Shields et al. | |
| 2017/0086823 A1 | 3/2017 | Leimbach et al. | |
| 2019/0125476 A1* | 5/2019 | Shelton, IV | F16D 27/09 |
| 2020/0222071 A1* | 7/2020 | Pak | A61B 17/2833 |

FOREIGN PATENT DOCUMENTS

| | | | |
|---|---|---|---|
| DE | 10155734 C1 | 4/2003 |
| DE | 10137915 B4 | 7/2004 |
| DE | 10321854 B3 | 12/2004 |
| DE | 102004033290 A1 | 2/2006 |
| DE | 102011007121 A1 | 10/2012 |
| EP | 1155776 A2 | 9/2006 |

OTHER PUBLICATIONS

Written Opinion received in International Application No. PCT/
EP2020/081251 dated Jan. 12, 2021, with translation, 17 pages.

\* cited by examiner

MEDICAL SLIDING SHAFT INSTRUMENT

CROSS-REFERENCE TO RELATED APPLICATIONS

This application is a continuation of International Application No. PCT/EP2020/081251, filed on Nov. 6, 2020, and claims priority to German Application No. 10 2019 130 223.4, filed on Nov. 8, 2019. The contents of International Application No. PCT/EP2020/081251 and German Application No. 10 2019 130 223.4 are incorporated herein by reference in their entireties and for all purposes.

FIELD

The present disclosure relates to medical sliding shaft instruments generally, and more specifically to a medical sliding shaft instrument comprising a tool element carrier, a tubular sliding shaft surrounding the tool element carrier and defining a sliding direction, and an actuating device for moving the sliding shaft relative to the tool element carrier in the distal direction, wherein at least one tool element is arranged or movably mounted on the distal end of the tool element carrier, wherein the at least one tool element is arranged or formed so as to cooperate with a distal end region of the sliding shaft in such a way that the at least one tool element is moved as a result of a movement of the sliding shaft in the distal direction, wherein the instrument further comprises a locking device for blocking a movement of the sliding shaft relative to the tool element carrier in at least one advancing position, wherein the sliding shaft in the at least one advancing position is displaced in the distal direction in relation to a basic position in which the sliding shaft is displaced to a maximum extent in the proximal direction relative to the tool element carrier, wherein the locking device defines a release position in which the sliding shaft is displaceable, in particular in the proximal direction, relative to the tool element carrier, and a locking position in which a movement of the sliding shaft relative to the tool element carrier in the proximal and/or distal direction is blocked, wherein the locking device comprises at least one first locking element and at least one second locking element, which in the locking position are in force-locking and/or positive-locking engagement and in the release position are out of engagement.

BACKGROUND

Medical sliding shaft instruments are disclosed, e.g., in DE 101 55 734 C1 or in DE 103 21 854 B3. The sliding shaft instruments described in these publications may optionally be equipped with a lock in the form of a locking device described at the outset in order to hold the sliding shaft relative to the tool element carrier in an advancing position, for example temporarily. This means that a movement of the sliding shaft relative to the tool element carrier in the distal and/or proximal direction is blocked when the locking device is active, i.e., adopts the locking position.

Conventional locking devices comprise, e.g., two locking elements projecting on branches of the actuating device, which are typically made of a thin sheet metal and are welded onto branches. Locking devices of that kind are prone to needing frequent repairs due to their structure and can be deformed by improper use and handling, which can lead to malfunction of the locking device.

SUMMARY

In a first aspect, a medical sliding shaft instrument comprises a tool element carrier, a tubular sliding shaft surrounding the tool element carrier and defining a sliding direction, and an actuating device for moving the sliding shaft relative to the tool element carrier in the distal direction. At least one tool element is arranged or movably mounted on the distal end of the tool element carrier. The at least one tool element is arranged or formed so as to cooperate with a distal end region of the sliding shaft in such a way that the at least one tool element is moved as a result of a movement of the sliding shaft in the distal direction. The sliding shaft instrument further comprises a locking device for blocking a movement of the sliding shaft relative to the tool element carrier in at least one advancing position. The sliding shaft in the at least one advancing position is displaced in the distal direction in relation to a basic position in which the sliding shaft is displaced to a maximum extent in the proximal direction relative to the tool element carrier. The locking device defines a release position in which the sliding shaft is displaceable, in particular in the proximal direction, relative to the tool element carrier, and a locking position in which a movement of the sliding shaft relative to the tool element carrier in the proximal and/or distal direction is blocked. The locking device comprises at least one first locking element and at least one second locking element, which in the locking position are in force-locking and/or positive-locking engagement and in the release position are out of engagement. The at least one second locking element is arranged or formed on the sliding shaft and the at least one first locking element is transferable from the release position into the locking position by a movement toward the sliding shaft.

BRIEF DESCRIPTION OF THE DRAWING FIGURES

Figure 2:
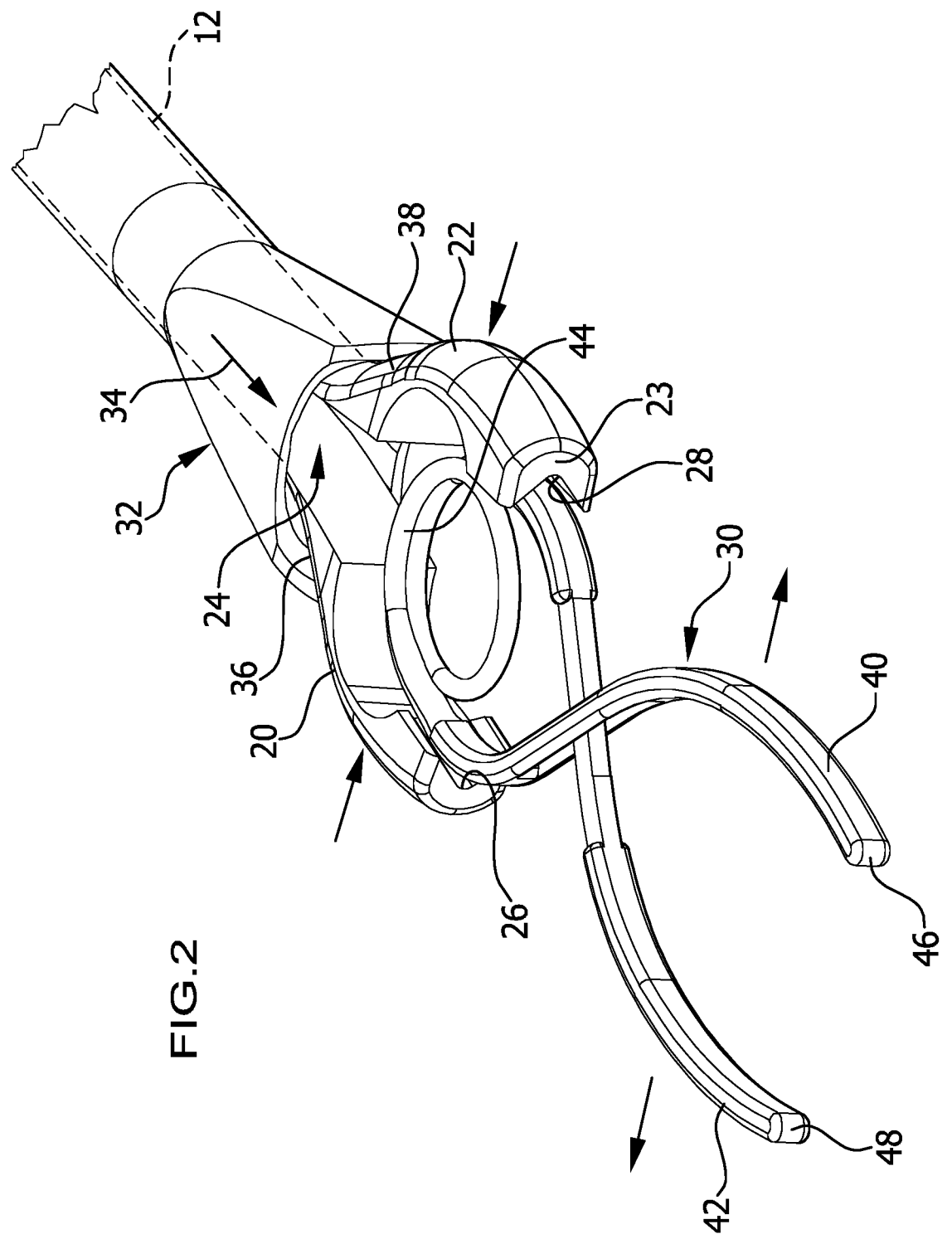
Figures 3, 4:
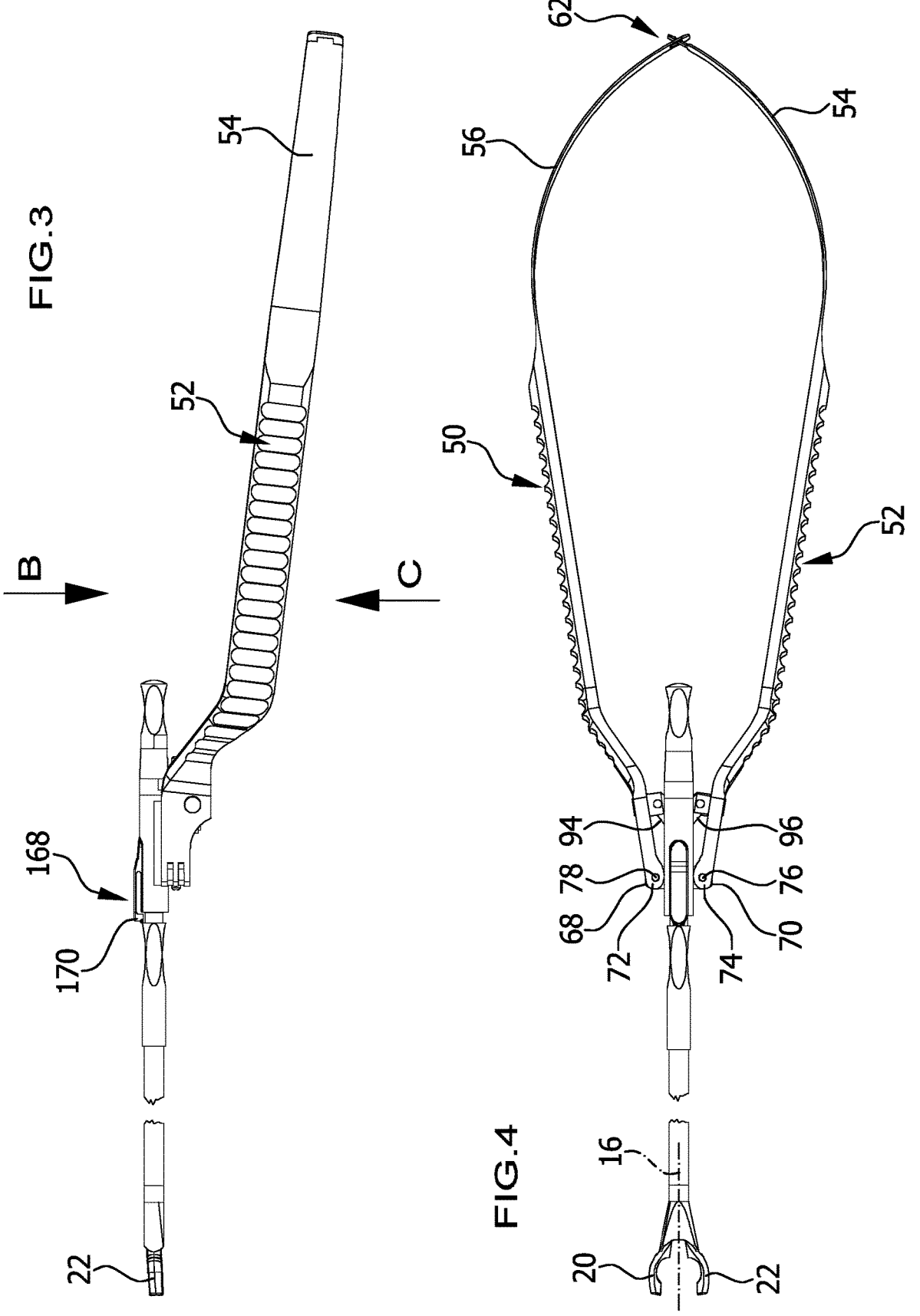
Figures 5, 6:
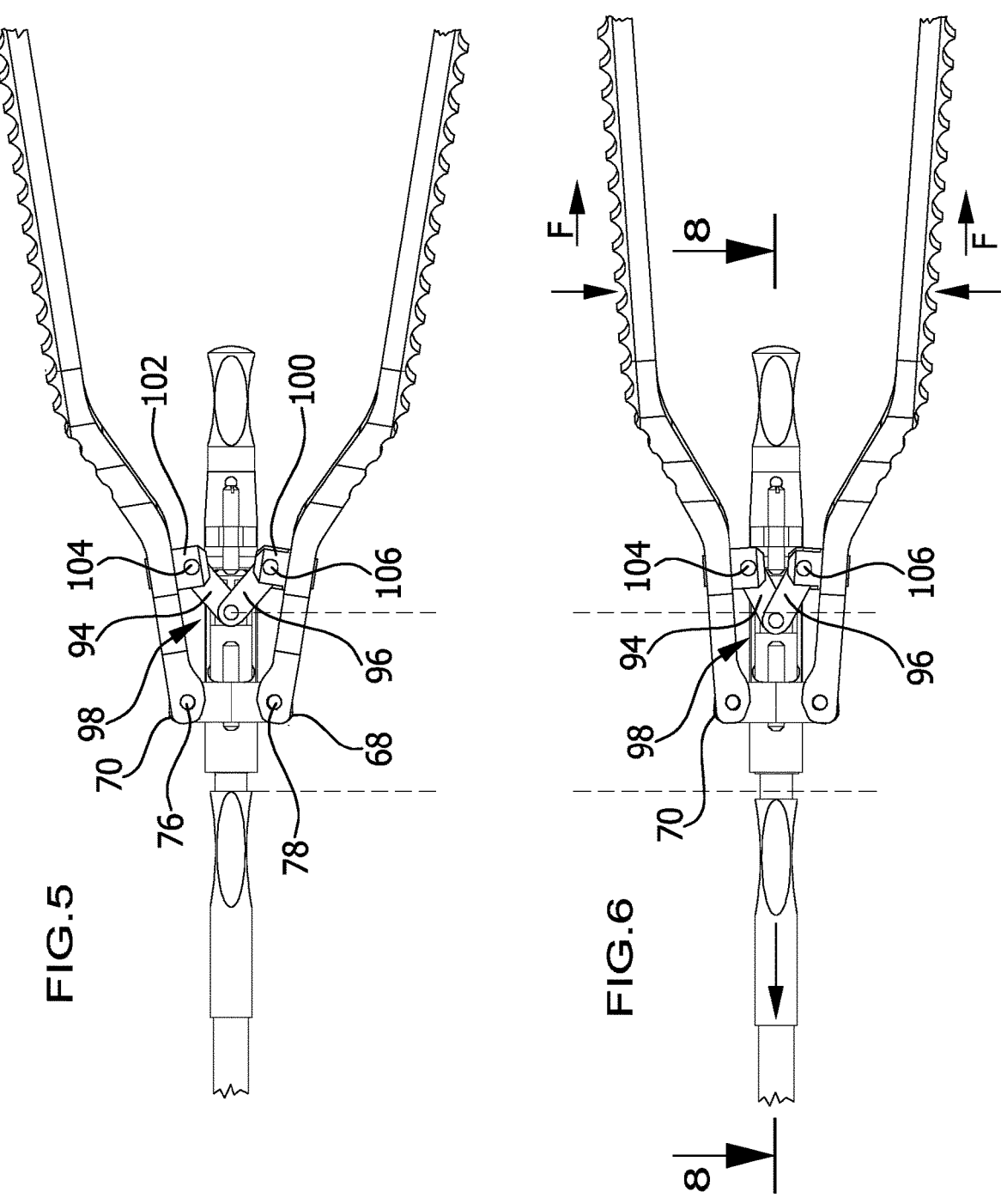
Figure 7:
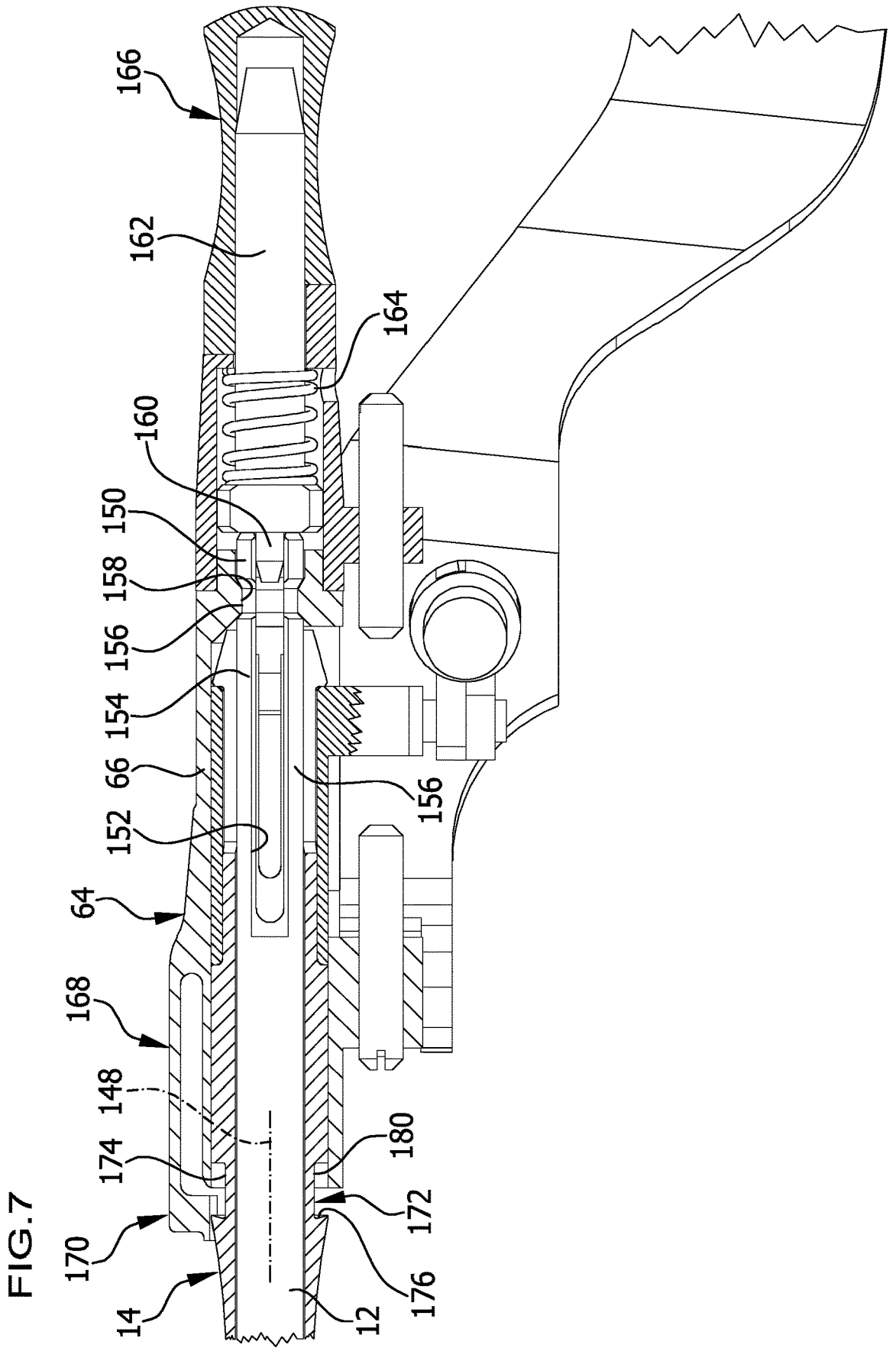
Figure 8:
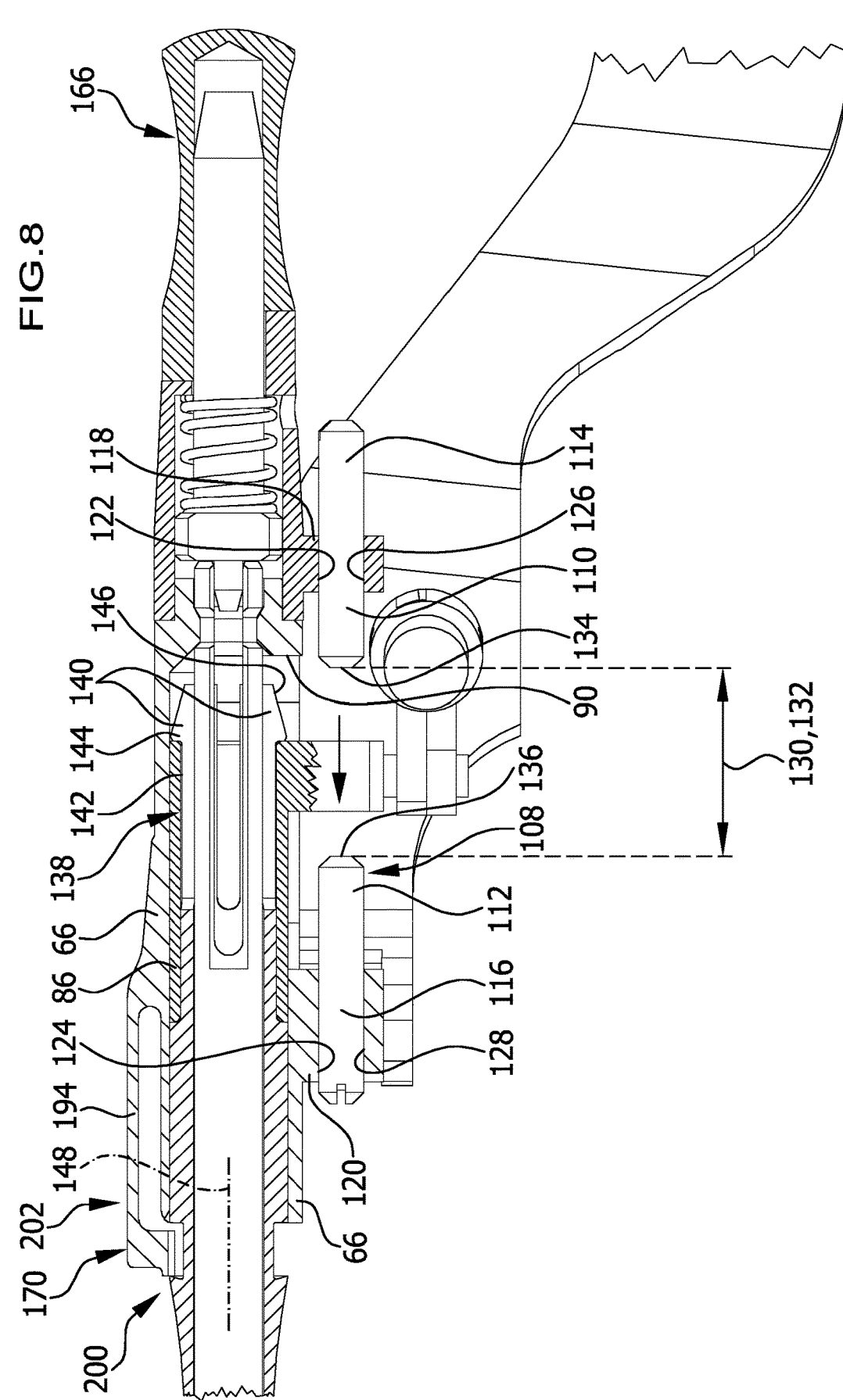
Figure 9:
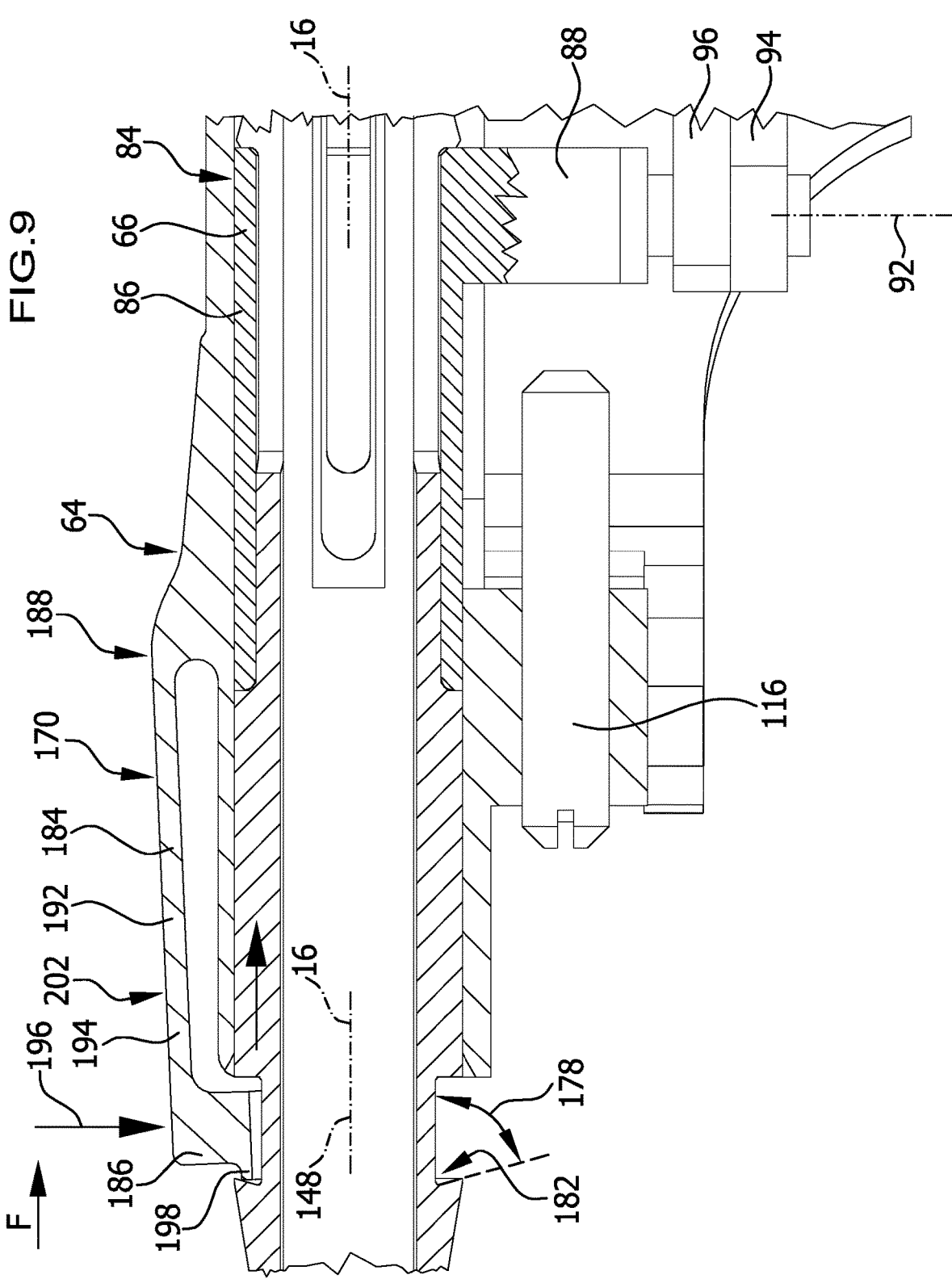
Figure 10:
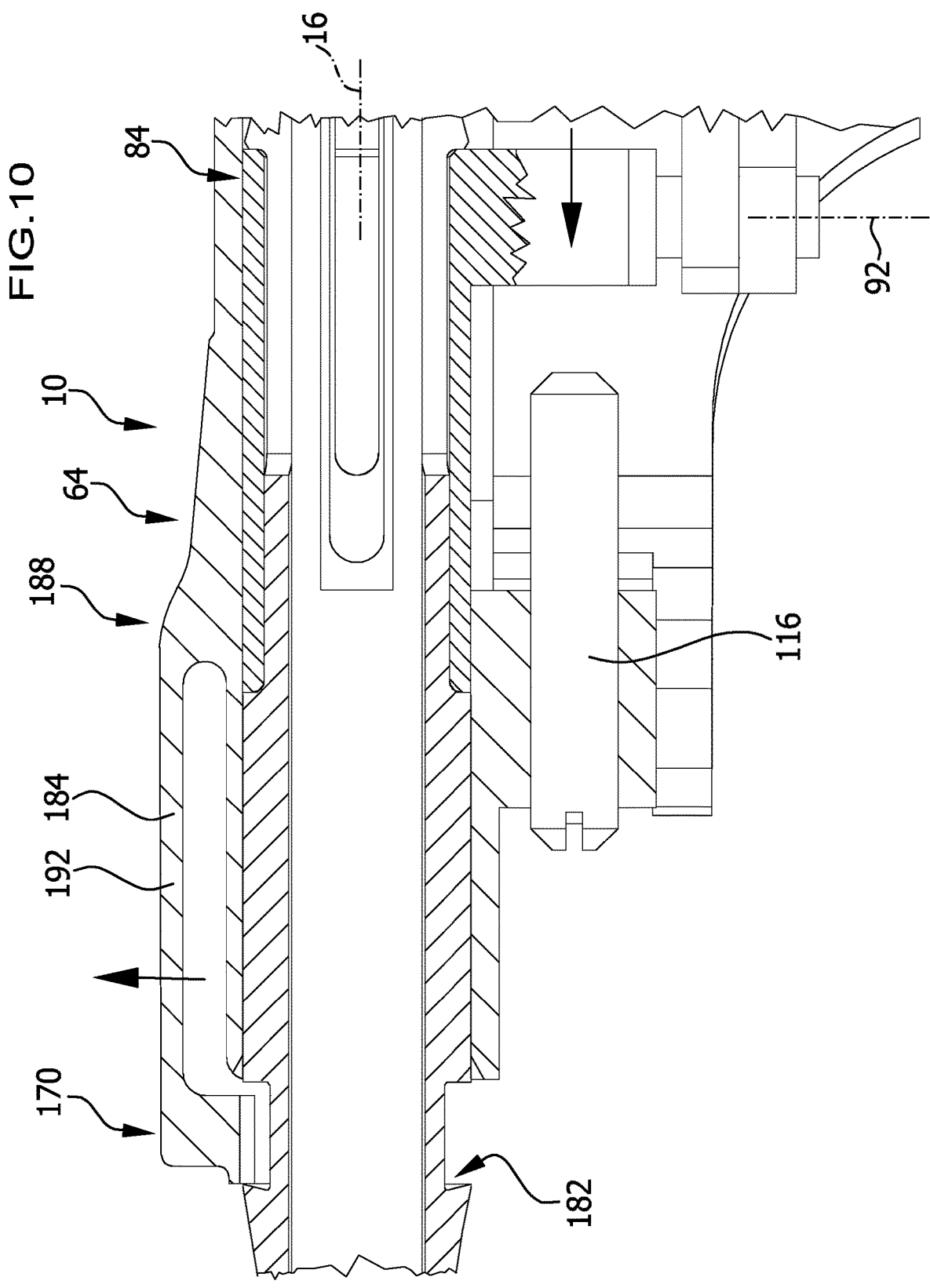
Figure 11:
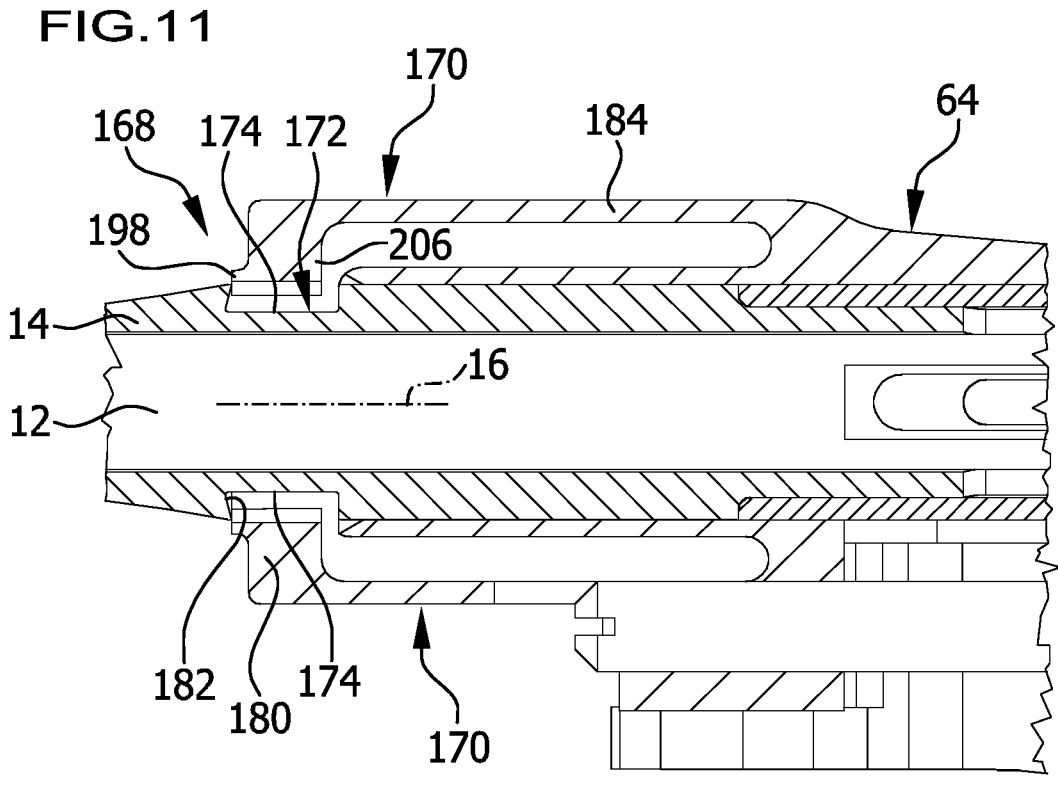
Figure 12:
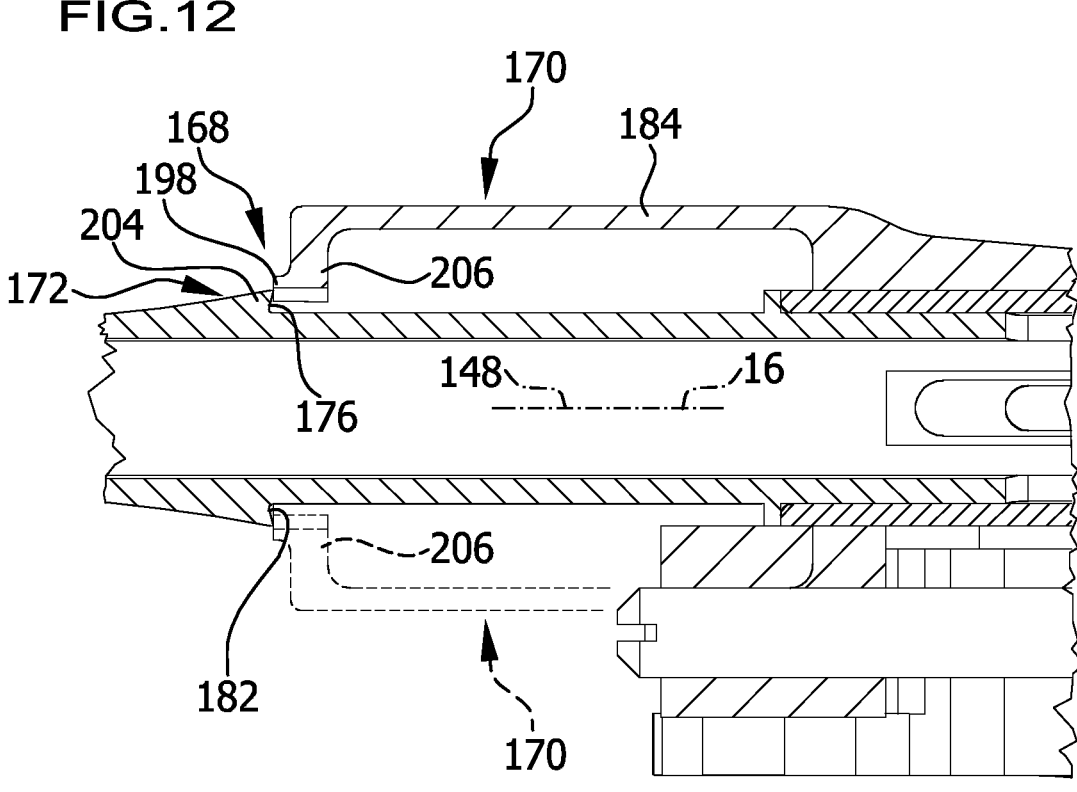
Figure 13:
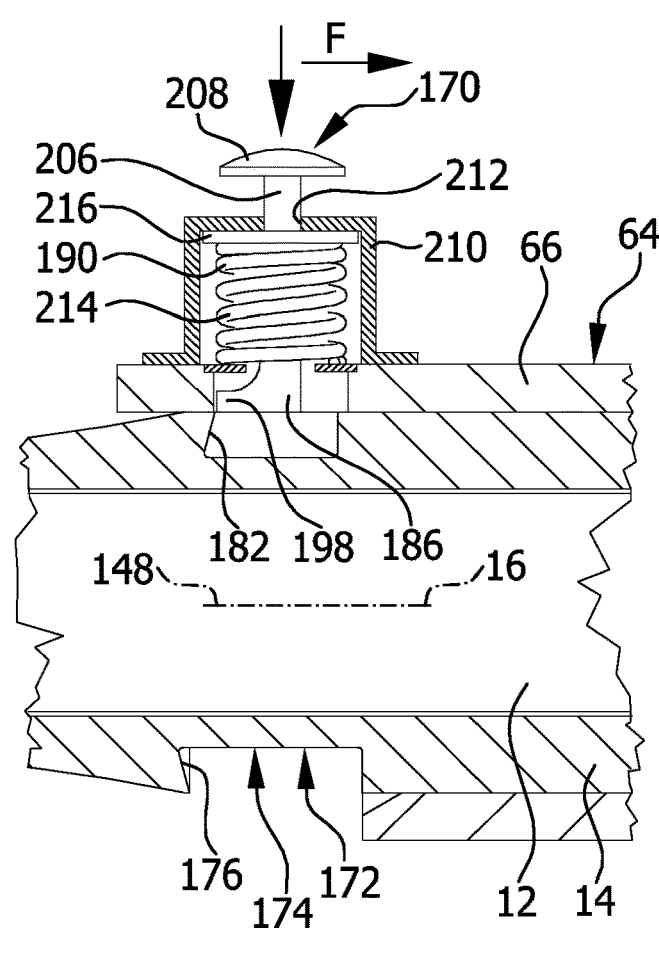
Figure 14:
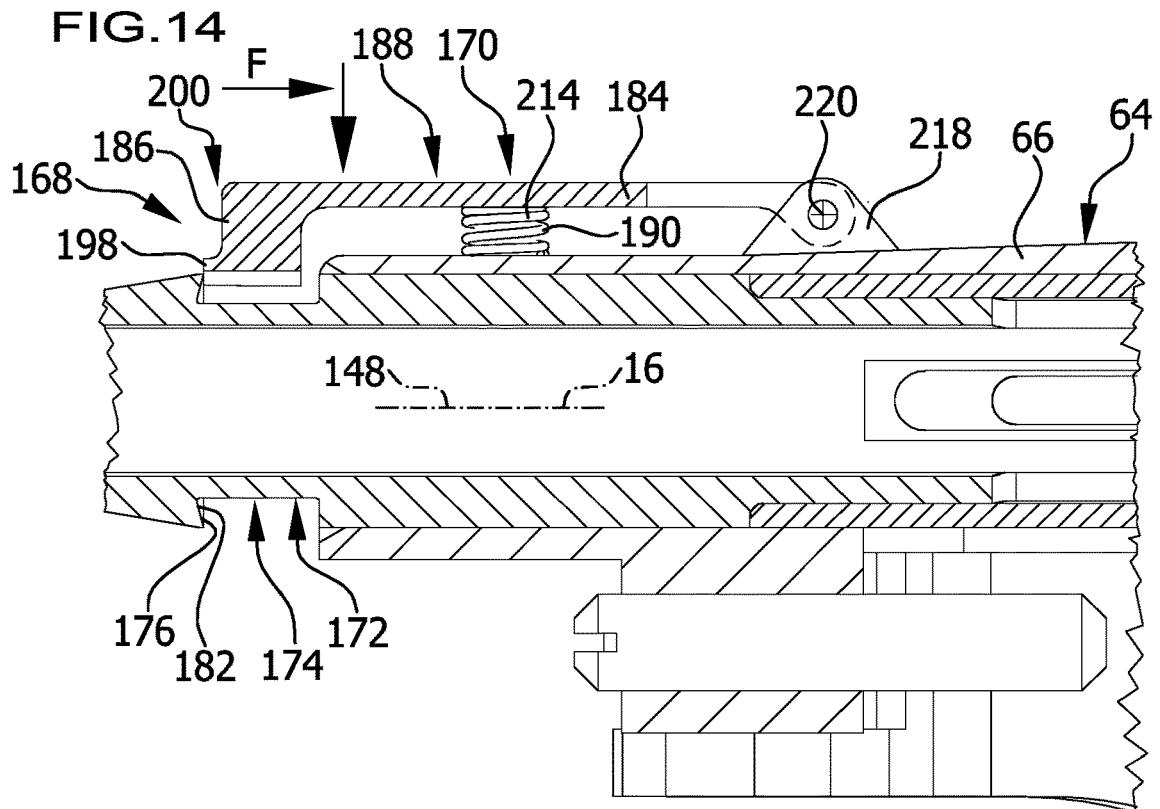

The foregoing summary and the following description may be better understood in conjunction with the drawing figures, of which:

FIG. 1: shows a schematic perspective total view of an embodiment of a sliding shaft instrument;

FIG. 2: shows an enlarged partial view of the region A from FIG. 1 with a surgical clip held on the sliding shaft instrument;

FIG. 3: shows a side view of the sliding shaft instrument from FIG. 1;

FIG. 4: shows a view of the sliding shaft instrument from FIG. 3 in the direction of the arrow B;

FIG. 5: shows a partial view of the sliding shaft instrument from FIG. 3 in the direction of the arrow C;

FIG. 6: shows a view similar to FIG. 5 with the sliding shaft moved somewhat in the distal direction relative to the tool element carrier;

FIG. 7: shows a sectional longitudinal view of the sliding shaft instrument with a sliding shaft deflected from the basic position before reaching the locking position;

FIG. 8: shows a cut view of the sliding shaft instrument from FIG. 6 along line 8-8;

FIG. 9: shows an enlarged partial view of the arrangement from FIG. 9 with the locking elements interengaging;

FIG. 10: shows an enlarged view of a part of the arrangement from FIG. 8;

FIG. 11: shows a view similar to FIG. 10 of a further embodiment of a sliding shaft instrument;

FIG. 12: shows a view similar to FIG. 10 of a further embodiment of a sliding shaft instrument;

FIG. 13: shows a view similar to FIG. 10 of a further embodiment of a sliding shaft instrument; and FIG. 14: shows a view similar to FIG. 10 of a further embodiment of a sliding shaft instrument.

DETAILED DESCRIPTION

Although the present disclosure refers to specific embodiments, the present disclosure is not intended to be limited to the details shown. Rather, various modifications may be made in the details within the scope and range of equivalents and without departing from the present disclosure.

The present disclosure relates to a medical sliding shaft instrument comprising a tool element carrier, a tubular sliding shaft surrounding the tool element carrier and defining a sliding direction, and an actuating device for moving the sliding shaft relative to the tool element carrier in the distal direction, wherein at least one tool element is arranged or movably mounted on the distal end of the tool element carrier, wherein the at least one tool element is arranged or formed so as to cooperate with a distal end region of the sliding shaft in such a way that the at least one tool element is moved as a result of a movement of the sliding shaft in the distal direction, wherein the sliding shaft instrument further comprises a locking device for blocking a movement of the sliding shaft relative to the tool element carrier in at least one advancing position, wherein the sliding shaft in the at least one advancing position is displaced in the distal direction in relation to a basic position in which the sliding shaft is displaced to a maximum extent in the proximal direction relative to the tool element carrier, wherein the locking device defines a release position in which the sliding shaft is displaceable, in particular in the proximal direction, relative to the tool element carrier, and a locking position in which a movement of the sliding shaft relative to the tool element carrier in the proximal and/or distal direction is blocked, wherein the locking device comprises at least one first locking element and at least one second locking element, which in the locking position are in force-locking and/or positive-locking engagement and in the release position are out of engagement, wherein the at least one second locking element is arranged or formed on the sliding shaft and wherein the at least one first locking element is transferable from the release position into the locking position by a movement toward the sliding shaft.

The proposed further development makes it possible, in particular, to lock the sliding shaft instrument in the at least one advancing position, i.e., for example to block a movement of the sliding shaft relative to the tool element carrier in the proximal direction. The arrangement of the at least one second locking element on the sliding shaft or the formation thereof directly on the sliding shaft simplifies the structure of the instrument. The at least one second locking element can thus, for example, be formed in one piece in the sense of monolithically with the sliding shaft. This is not possible with conventionally used locking devices. The stability of the sliding shaft instrument and thus the handleability thereof can thereby be improved. This transferring of the sliding shaft instrument from the release position of the locking device into the locking position is achieved by a movement of the at least one first locking element toward the sliding shaft. This enables, in particular, a handling that is particularly simple and secure for the user, as they engage with the at least one first locking element directly on the sliding shaft to lock the sliding shaft instrument. In particular, such a sliding shaft instrument can formed without the locking elements having to be arranged or formed on the actuating device. In particular, the likelihood of an unintentional actuation of the locking device can thereby be minimized. With such a locking device, it is possible, in particular, to hold the at least one tool element, for example two tool elements, in a defined, partially closed position. If the sliding shaft instrument is configured in the form of a clip applier, thus, in particular, a small aneurysm clip defined with a slightly opened mouth can be securely held and the sliding shaft instrument with a clip held thereby can be securely passed to a surgeon by a person assisting them. The proposed arrangement of the locking elements enables, in particular, an arrangement or formation of the locking device that is mirror-symmetrical in relation to a plane containing the sliding direction. This makes it possible, in particular, to make the sliding shaft instrument and thus also the locking device securely usable both for left- and right-handed users.

It is advantageous if the at least one second locking element and the sliding shaft are formed in one piece. In particular, they may be formed monolithically. The sliding shaft instrument can thus be produced significantly more simply, thereby making it possible to improve productivity and a process security in the production of the sliding shaft instrument. Due to the one-piece configuration of the second locking element and the sliding shaft, the locking device can be configured to be significantly less susceptible to needing repairs in comparison to conventional locking devices, which leads to a longer service life and thus to a longer lifetime of the sliding shaft instrument.

It is favorable if the at least one first locking element is movable in a direction transverse, in particular perpendicular, to the sliding direction from the release position into the locking position. Such a configuration makes it possible, in particular, to engage with the at least one first locking element directly on the sliding shaft and to block a displacement of the sliding shaft relative to the tool element carrier in the proximal and/or distal direction.

It is advantageous if the at least one first locking element is arranged or formed on the sliding shaft instrument and so as to be immovable or substantially immovable relative to the tool element carrier in the sliding direction. This is to be understood to mean, in particular, that the at least one first locking element is not movable in, e.g., an axial direction that is defined by the tool element carrier or by the sliding shaft, but rather only transversely hereto. Substantially immovable means that, for example, a lever or lever arm that extends in parallel to the sliding direction and is comprised by the first locking element or is arranged or formed on the at least one first locking element is substantially immovable in the sliding direction when the lever can be pivoted or deformed with a free end in the direction toward the sliding shaft in order to transfer the locking device from the release position into the locking position and vice versa.

The handling of the sliding shaft instrument can be achieved for a user in the usual way if the actuating device comprises two actuating elements that are movable relative to one another. In particular, the two actuating elements may be arranged or formed so as to be pivotable relative to one another.

For a particularly sensitive handling of the sliding shaft instrument, it is advantageous if the two actuating elements, when the sliding shaft is displaced to a maximum extent in the proximal direction, are at a maximum distance from one another and are movable toward one another for moving the sliding shaft in the distal direction. The actuating elements are thus moved toward one another, i.e., pressed against one another, in order to move the sliding shaft in the distal direction. The basic position of the at least one tool element is defined, as already explained, by the sliding shaft being displaced relative to the tool element carrier to a maximum extent in the proximal direction.

The sliding shaft instrument can be configured in a particularly simple manner if the two actuating elements are each pivotable about a pivot axis, which extends transversely to the sliding direction. In particular, the pivot axes may extend perpendicularly to the sliding direction. For example, the two actuating elements may be mounted so as to be pivotable independently of one another, such that they each define a pivot axis. Said axes may extend in parallel or, in the case of a common articulation, may also coincide.

In accordance with a further preferred embodiment, provision may be made that the sliding shaft instrument comprises for a biasing device for exerting a biasing force acting in the proximal direction on the sliding shaft. Such a biasing device makes it possible, in particular, when the instrument is not actuated, i.e., when no forces are being exerted by the user on the actuating device and the locking device adopts the release position, to slide the sliding shaft relative to the tool element carrier to a maximum extent in the proximal direction. In this position, for example, the at least one tool element can adopt its one extreme position. If, for example, two tool elements are provided, they may then be opened to a maximum extent or closed to a maximum extent, depending on for which application the sliding shaft instrument is intended.

It is advantageous if the biasing device comprises at least one biasing element and if the two actuating elements are movable toward one another against the action of the at least one biasing element. A design of that kind makes it possible, in particular, to configure the sliding shaft instrument in such a way that a defined actuating force is required to slide the sliding shaft in the distal direction. In addition, such a biasing device makes it possible to automatically transfer the sliding shaft instrument back into the basic position when the locking device is not actuated, i.e., adopts the release position.

The at least one second locking element favorably comprises a stop face that faces in the proximal direction. This makes it possible, in particular, to block a movement of the sliding shaft relative to the tool element carrier in the proximal direction when the at least one first locking element engages on the stop face. If the sliding shaft instrument comprises a biasing device, the latter can hold, e.g., the at least one first locking element, which is slid toward the sliding shaft and is in abutment against the stop face, and the second locking element cooperating therewith in force-locking engagement.

In order to prevent an unintentional release of the sliding shaft instrument, i.e., the transfer of the locking device from the locking position into the release position, it is favorable if the at least one second locking element has an undercut and if the undercut is delimited at least partially by the stop face. The configuration of the at least one second locking element can thus be realized in a simple manner. When said second locking element engages at least partially into the undercut, first a movement of the sliding shaft in the distal direction is required to release the locking device. An unintentional opening or closing of two cooperating tool elements on the distal end of the tool element carrier can thus be prevented, in particular when the sliding shaft instrument is being passed or handed over to a surgeon by a person assisting them.

The sliding shaft instrument can be configured in a simple manner if the stop face is inclined in the direction toward the sliding shaft. Such a stop face can be formed in one piece on the sliding shaft in a simple manner.

To be able to achieve a secure function of the locking device, it is favorable if an angle of inclination between the stop face and the sliding direction is in a range of about 88° to about 60°. An undercut formed in that way can be easily produced and can also be cleaned in a simple and secure manner.

It is advantageous if the at least one second locking element is configured in the form of a retaining projection from the sliding shaft, said retaining projection pointing in the radial direction, or in the form of a retaining groove that is open facing away from the sliding shaft. Both the retaining projection and the retaining groove may be configured, in particular, with stop faces that face in the proximal direction. Both can thus be arranged or formed on a sliding shaft in a simple manner.

The at least one second locking element preferably annularly surrounds the sliding shaft. In particular, the at least one second locking element is of self-enclosed configuration. Thus, for example, a retaining groove in the form of an annular groove or a retaining projection in the form of an annular projection can be formed on the sliding shaft. This makes it possible, in particular, to transfer the locking device from the release position into the locking position independently of a rotational position of the sliding shaft relative to the tool element carrier about the sliding direction or a longitudinal direction defined by said sliding shaft and the tool carrier due to a secure engagement of the at least one first locking element and the at least one second locking element.

In accordance with a further preferred embodiment, provision may be made that the locking device comprises a restoring device in such a way that the at least one first locking element is movable against the action of the restoring device from the release position into the locking position. This design requires an active actuation of the locking device against the action of the restoring device. An accidental actuation of the locking device can thus be avoided. Further, it is possible, in particular, to configure the locking device in such a way that it automatically transitions from the locking position into the release position when the at least one first locking element and the at least one second locking element are brought out of engagement. If, for example, the at least one second locking element is configured with an undercut that is open facing in the proximal direction, the locking device can be automatically released by the sliding shaft being slid relative to the tool element carrier somewhat in the distal direction. The locking elements then come out of engagement and the restoring device moves the at least one first locking element back into its basic position, for example into the release position in which the locking elements are out of engagement.

The restoring device can be configured in a simple manner if it comprises at least one restoring element, which is arranged or formed cooperating with the at least one first locking element. For example, the at least one restoring element may engage on the locking element or be comprised thereby.

The sliding shaft instrument can be configured in a simple manner if the at last one restoring element comprises a spring element. In particular, the spring element may be configured in the form of a coil spring or a leaf spring.

It is favorable if the at least one first locking element comprises a locking projection pointing in the direction toward the sliding shaft, which in the locking position is in engagement with the at least one second locking element.

The at least one first locking element can thus be optimally adapted to the sliding shaft and the second locking element arranged or formed thereon.

The at least one first locking element preferably comprises a latching nose, which in the locking position engages in a positive-locking or substantially positive-locking manner into the undercut on the at least one second locking element. A locking of the locking device in the locking position can thus be achieved in a simple manner, namely in particular when the sliding shaft instrument comprises a biasing device for exerting a biasing force acting in the proximal direction on the sliding shaft. This makes it possible, in particular, to hold the latching nose, which engages into the undercut, under pretension in this engagement position, and thus to hold the locking device in the locking position.

In order to, in particular, prevent a movement of the sliding shaft relative to the tool element carrier in the proximal direction in a simple and secure manner, it is advantageous if the latching nose is arranged or formed pointing in the distal direction. In particular, the latching nose may be arranged or formed on the locking projection.

It is favorable if the at least one first locking element comprises a lever arm and if the locking projection is arranged or formed on a free end of the lever arm. The locking projection can thus be moved, for example, in the direction toward the sliding shaft when the lever arm is pivoted or deformed with its free end in the direction toward the sliding shaft.

For a simple and secure handling of the sliding shaft instrument, it is favorable if the lever arm is arranged or formed on the instrument pointing in the distal direction. This enables, in particular, in a simple manner an arrangement of a latching nose pointing in the distal direction on the free end of the lever arm, for example on the locking projection arranged on the free end of the lever arm.

It is advantageous if the lever arm is fixed to the instrument on the proximal side. In particular, it may be mounted so as to be pivotable about a lever arm pivot axis, which extends, in particular, transversely, for example perpendicularly, to the sliding direction. This design makes it possible, in particular, to configure the at least one first locking element in the form of a pawl in a simple manner. The lever arm may be formed on the proximal side and in one piece on the sliding shaft instrument, i.e., monolithically therewith. An additional mounting of the lever arm can thus be avoided. This simplifies the structure of the instrument and thus the stability thereof.

The lever arm preferably comprises or forms the at least one restoring element. For example, the lever arm may form a resilient leaf spring element, on the free end of which the locking projection is arranged. An end of the lever arm facing in the proximal direction may be arranged on the sliding shaft instrument.

The at least one first locking element preferably comprises a locking element portion extending transversely to the sliding direction. For example, the locking element portion may be configured and arranged in such a way that, in the locking position, it cooperates with the at least one second locking element.

It is favorable if the at least one restoring element is arranged or formed surrounding the locking element portion. This makes it possible, in particular, to configure the at least one first locking element in the form of a valve pusher in a simple manner.

It is favorable if the locking projection is arranged or formed on an end of the locking element portion pointing toward the sliding shaft. Thus, in particular, only the part of the locking element portion that cooperates with or engages into the at least one second locking element defines the locking projection.

It is advantageous if the sliding shaft instrument comprises a securing device for securing the locking device in the locking position. By means of such a securing device, it can be avoided, in particular, that the sliding shaft instrument is able to automatically transition from the locking position into the release position. Thus, in order to release the locking device, first the securing device must be released.

The sliding shaft instrument can be configured in a simple manner if the securing device comprises the at least one first locking element and the at least one second locking element, which are arranged or formed in such a way that the locking device is releasable only through a movement of the sliding shaft in the distal direction. The securing device can thus, in particular, be integrated into the locking device, for example by means of special design of the locking elements. They may be configured, in particular, in the described manner, such that the locking position is transferable into the release position when the sliding shaft is first moved somewhat in the distal direction relative to the tool element carrier. This can be achieved by means of a special design of the locking elements, which do not enable a simple disengagement only by a movement relative to one another in the radial direction.

The securing device can be configured in a simple manner if it comprises the undercut and the latching nose. When these are configured in such a way that they act pointing in the distal direction and proximal direction, respectively, they form two cooperating securing elements, which are comprised by the securing device and can be brought out of engagement only by a relative movement of the sliding shaft and the tool element carrier in the distal direction, in order to then transfer the locking elements from the locking position into the release position.

It is favorable if the sliding shaft instrument comprises a stop device for delimiting a movement of the sliding shaft in the proximal direction and in the distal direction. Thus, for example, damage to implants, for example aneurysm clips, that are to be handled by the sliding shaft instrument can be prevented in a simple and secure manner. The maximum sliding positions of the sliding shaft and the tool element carrier defined by the stop device relative to one another then also define extreme positions of the at least one tool element on the distal end of the tool element carrier.

It is advantageous if the stop device comprises a proximal stop and a distal stop and if a maximum displacement path of the sliding shaft relative to the tool element carrier is defined by a distance of active surfaces of the proximal stop and the distal stop from one another. For example, the active surfaces of the stops may face toward one another. The displacement path is then defined by the spacing of these active surfaces. Optionally, the stops may also be of adjustable configuration. This makes it possible, in particular, to adjust the instrument at the factory or optionally for a user to readjust the instrument in order to be able to specify in a desired manner the extreme positions of the sliding shaft and thus extreme positions of the at least one tool element on the distal end of the tool element carrier.

The proximal stop preferably defines the basic position and the distal stop preferably defines a position of the sliding shaft deflected to a maximum extent in the distal direction. A use of the sliding shaft instrument can thus be preset in the desired manner by the arrangement and positioning of the stops.

It is favorable if the locking device blocks a movement of the sliding shaft relative to the tool element carrier in at least one advancing position between the basic position and the maximally deflected position in the distal direction. It is thus possible, in particular, to lock the sliding shaft instrument with the locking device in a defined deflected position of the at least one tool element. For example, it may be a partially opened or partially closed position of mutually cooperating jaw parts of the sliding shaft instrument, said jaw parts defining two or more tool elements.

In order to improve the cleanability of the sliding shaft instrument, it is advantageous if the tool element carrier is coupled to the actuating device in a working position and is separated from the actuating device in a cleaning position.

The cleanability of the sliding shaft instrument can also be further improved by the sliding shaft being coupled to the actuating device in the working position and separated from the actuating device in the cleaning position.

It is favorable if the actuating device comprises a coupling part, if the two actuating elements are movably arranged on the coupling part, and if the tool element carrier is immovably held on the coupling part in the working position. Such a design can ensure, in particular, that a distal end of the tool element carrier is not moved in the sliding direction relative to the coupling part and thus to the actuating device. A surgeon can thus guide and hold the sliding shaft instrument in the usual manner. In particular, the at least one first locking element may be arranged or formed in one piece, for example monolithically, on the coupling part. A number of releasably connectable parts of the sliding shaft instrument can thus be minimized.

It is advantageous if the coupling part comprises a driving member mounted so as to be displaceable in the sliding direction and if the driving member is coupled to the two actuating elements by way of a connecting rod arrangement for moving the driving member in the sliding direction as the result of a movement of the two actuating elements toward one another or away from one another. For example, in the case of a demountable sliding shaft instrument, the sliding shaft can be brought with its proximal end into force-locking and/or positive-locking engagement with the driving member, such that said sliding shaft correspondingly moved upon a movement of the driving member.

It is advantageous if a proximal end of the sliding shaft in the working position is coupled to the driving member. Thus, in particular, the sliding shaft can be released from the actuating device by the proximal end thereof being decoupled from the driving member, such that the sliding shaft adopts the cleaning position in which it is separated from the actuating device.

It is advantageous if the at least one restoring element engages on the coupling part on the one hand and on the at least one first locking element on the other hand. In particular, it may engage on the lever arm of the at least one locking element. As a result of this arrangement of the at least one restoring element of the restoring device, it can be ensured, in particular, that the locking device is automatically transferred into the release position when the securing device is released.

The sliding shaft instrument can be secured in an advancing position in a particularly simple manner if the at least one first locking element is configured in the form of a pawl engaging on the sliding shaft in the locking position. The pawl may, in particular, be resiliently biased so that it is automatically transferred into the release position. In particular, the pawl may comprise the latching nose, which cooperates with an undercut on the sliding shaft, in particular on the at least one second locking element.

To be able to create any shaft form, it is advantageous if the sliding direction runs rectilinearly or in a curved manner. In particular, rectilinear sliding shaft instruments can then be formed, in which the sliding direction is defined by a longitudinal axis of the tool element carrier or a longitudinal axis of the sliding shaft. Alternatively a curved sliding direction can be defined by a curved tool element carrier and a correspondingly curved sliding shaft.

To be able to form a particularly compact sliding shaft instrument, it is advantageous if the at least one tool element and the tool element carrier are formed in one piece. Thus, in particular, movable mountings of the at least one tool element on the tool element carrier, which are expensive to produce, can be foregone.

Surgical clips, in particular aneurysm clips, can be handled with the sliding shaft instrument in a simple and secure manner if the sliding shaft instrument is configured in the form of a clip applier.

A first embodiment of a medical sliding shaft instrument is schematically depicted in FIG. 1 and is denoted as a whole with the reference numeral 10. It comprises a tool element carrier 12, which is surrounded by a tubular sliding shaft 14.

The sliding shaft 14 defines a sliding direction 16, namely by its longitudinal axis 148. The sliding direction 16 thus runs rectilinearly in the embodiment depicted in FIG. 1. Alternatively, in an embodiment that is not depicted, the sliding direction may also run in a curved manner.

The sliding shaft instrument 10 further comprises an actuating device 18 for moving the sliding shaft 14 relative to the tool element carrier 12 both in the distal and in the proximal direction.

In the depicted embodiment, two tool elements 20 and 22 are arranged on the distal end of the tool element carrier 12. They are formed in one piece, namely monolithically, with the tool element carrier 12. They are configured in the form of elongate arms, which, commencing from a distal end 23 of the tool element carrier 12, are separated from one another by a slit 24.

In a basic position in which no external forces are acting on them, the two tool elements 20, 22 are spread apart, as is schematically depicted in FIGS. 1 and 2.

The tool elements 20 and 22 have holding surfaces 26 and 28, which face toward one another and are of somewhat recessed configuration, in order to, for example, accommodate a surgical clip 30 that is schematically depicted in FIG. 2.

An end portion 32 of the sliding shaft 14 that widens in a funnel-like manner in the distal direction serves for closing the tool elements 20 and 22. When the sliding shaft 14 is moved in the distal direction, as is indicated in FIG. 2 by the arrow 34, the end portion 32 slides on mutually averted outer surfaces 36 and 38 of the tool elements 20 and 22 so that the latter are moved toward one another. As a result of this movement of the tool elements 20 and 22, the clip 30 accommodated between said tool elements is not only held clampingly, but also successively opened with increasing proximity of the tool elements 20 and 22 to one another. This functionality results in the case of the clip 30 from the fact that the clamping arms 40 and 42 thereof, which are connected on the proximal side to a helical spring element, cross. In other words, the clip 30 is configured in such a way that it adopts a closing position without external forces acting on it, in which closing position the clamping arms 40 and 42 adopt with their free ends 46 and 46 a position as close together as possible.

In the described manner, the tool elements 20 and 22 are arranged or formed cooperating with the end portion 32 of the sliding shaft 14 forming a distal end region in such a way that the tool elements 20 and 22 are moved, namely toward one another in the embodiment depicted, as the result of a movement of the sliding shaft in the distal direction.

In the case of the sliding shaft instrument 10, the actuating device 18 comprises two actuating elements 50 and 52, which are movable, namely pivotable, relative to one another. Proximal end portions of the actuating elements 50 and 52 configured in the form of branches are configured in the form of leaf spring-like biasing elements 54 and 56. Free ends 58 and 60 thereof are movably in engagement with one another. The biasing elements 54 and 56 form a biasing device 62 for exerting a biasing force acting in the proximal direction on the sliding shaft 14.

The biasing elements 54 and 56 are curved facing toward one another and in a basic position hold the actuating elements 50 and 52 in a position at a maximum distance from one another. When the actuating elements 50 and 52 are moved toward one another as schematically depicted by the arrows in FIG. 1, this occurs against the action of the biasing device 62, i.e., against the action of the biasing elements 54 and 56.

The actuating device 18 comprises a coupling portion 64, also referred to as coupling part, with a sleeve 66 from which bearing jaws 68 and 70, facing away from one another transversely to the sliding direction 16, project, on which ends 72 and 74, pointing in the distal direction, of the actuating elements 50 and 52 are pivotably mounted by means of bearing pins 76 and 78. The two bearing pins 76 and 78 each define a pivot axis 80 and 82, respectively, which extends transversely, perpendicularly in the case of the embodiment depicted in the Figures, to the sliding direction 16.

A driving member 84 that is mounted so as to be slidable in the sliding direction 16 is arranged in the sleeve 66. The driving member 84 comprises a sleeve portion 86 that is displaceably mounted in the sleeve 16, from which sleeve portion 86 a coupling pin projects from a window 90 configured in the form of a perforation that extends in the sliding direction 16.

Two connecting rods 94 and 96 of a connecting rod arrangement 98 are mounted on the coupling pin 88 so as to be pivotable about a common pivot axis 92 that extends in parallel to the pivot axes 80 and 82. The respective other ends of the connecting rods 94 and 96 are each pivotably mounted on the proximal side of the bearing jaws 68 and 70 on bearing jaws 100 and 102, respectively, which are arranged facing toward one another projecting from the actuating elements 50 and 52, by means of bearing pins 104 and 106, respectively. The bearing pins 104 and 106 define with their longitudinal axes pivot axes that extend in parallel to the pivot axis 92.

Due to the coupling of the actuating elements 50 and 52 in the described manner to the coupling pin 88 of the driving member 84 by means of the connecting rod arrangement 98, the driving member 84 is moved in the distal direction when the actuating elements 50 and 52 are moved toward one another and is moved in the proximal direction when the actuating elements 50 and 52 are moved away from one another.

The sliding shaft instrument 10 further comprises a stop device 108 for delimiting a movement of the sliding shaft 14 in the proximal direction and in the distal direction. For this purpose, the stop device 108 comprises a proximal stop 110 and a distal stop 112. The stops 110 and 112 are formed by grub screws 114 and 116, respectively, provided with an external thread, which are screwed into bores 126 and 128, provided with internal threads 122 and 124, respectively, and extending in parallel to the sliding direction 16, on stop projections 118 and 120 projecting from the sleeve 66 in parallel to the coupling pin 88.

A maximum displacement path 130 of the driving member 84 relative to the sleeve 66 is defined by a distance 132 of active surfaces 134 and 136 of the proximal stop 110 and the distal stop 112 from one another. In the embodiment depicted in the Figures, the active surfaces 134 and 136 face toward one another and serve to delimit a movement of the coupling pin 88 in the proximal and distal direction, respectively.

The sliding shaft 14 in a basic position of the sliding shaft instrument 10 is displaced by means of the biasing device 62 to a maximum extent in the proximal direction. The proximal stop 110 defines the basic position. The distal stop 112 defines a maximally deflected position of the sliding shaft 14 in the distal direction.

The sliding shaft 14 in a working position is coupled to the actuating device 18. To make this possible, a proximal end portion 138 of the sliding shaft 14 is provided with two slits perpendicular to one another thereby forming four spring arms 140 extending in parallel to the sliding direction 16.

Formed on the spring arms facing outwardly away in the radial direction is an annular recess 142, into which the sleeve portion 86 engages in the working position. An outer surface of an annular projection 144 that adjoins the recess 142, which is configured in the form of an annular groove, has sliding surfaces 146 inclined in the proximal direction.

When the sliding shaft 14, from a cleaning position in which it is completely separated from the actuating device 18, is inserted with spring arms 140 in the proximal direction into the sleeve portion 86 of the driving member 84, the sliding surfaces 146 slide on the sleeve portion 86, such that the free ends of the spring arms 140, which point in the proximal direction, are pivoted in the direction toward the longitudinal axis 148 of the sliding shaft 14.

The spring arms 140 pivot back outwards away from the longitudinal axis 148 once the sleeve portion 86 is completely accommodated in the annular recess 142. The sliding shaft 14 is thus coupled to the driving member 84 of the actuating device 18 in the working position.

The tool element carrier 12 is provided with a slit 152 commencing from a proximal end 150. Thus, like on the sliding shaft 14, two spring arms 154 are formed on the tool element carrier 12, which extend in parallel to the longitudinal axis 148 facing in the proximal direction. Spaced somewhat at a distance from the end 150, an annular groove 156 is formed on the spring arms 154, into which an annular projection 158 projecting in the direction toward the longitudinal axis 148 engages when the tool element carrier 12 is coupled to the coupling portion 64.

An outer diameter of the tool element carrier 12 is adapted to an inner diameter of the sliding shaft 14, such that after coupling the sliding shaft 14 to the driving member 84 in the manner described above, the tool element carrier 12 can be slid commencing from the distal direction with the end 150 in the proximal direction through the sliding shaft 14. The end 150 slides on the annular projection 150, such that the spring arms 154 are pivoted toward one another until the annular projection 158 can dip into the annular groove 156.

To secure the tool element carrier 12 and the sliding shaft 14 in the described working position, a locking pin 160 is displaceably mounted on the coupling portion 64. The locking pin 160 projects from a push member 162 pointing in the distal direction. The push member 162 is biased in the distal direction by a biasing element 164 in the form of a coil spring.

The locking pin 160 is dimensioned such that in the working position it dips between the spring arms 154 of the tool element carrier 12 into the slit 152, thereby preventing a movement of the spring arms 154 toward one another. As a result of this positioning of the spring arms 154 in the working position, a pivoting of the spring arms 140 of the sliding shaft 14 in the direction toward the longitudinal axis 148 is simultaneously prevented by the spring arms 154. The locking pin 160 thus directly locks the tool element carrier 12 in the working position on the coupling portion 64 of the actuating device 18 and indirectly locks the sliding shaft 14 on the driving member 84 of the actuating device 18.

For disassembling the sliding shaft instrument 10, the push member 162, the proximal end of which is surrounded by a cap 166, is slid in the proximal direction against the action of the biasing element 164 in parallel to the longitudinal axis 148. The locking pin 160 then releases the spring arms 154, such that the tool element carrier 12 can be pulled out of the sliding shaft 14 in the distal direction.

When the tool element carrier 12 is pulled out of the sliding shaft 14, the spring arms 140 can be pivoted in the direction toward the longitudinal axis 140 by the sliding shaft 14 being pulled in the distal direction.

As a result of the coupling of the tool element carrier 12 to the actuating device 18 in the described manner, the tool element carrier 12 in the working position is immovably held on the coupling portion 64.

The sliding shaft instrument 10 further comprises a locking device 168 for blocking a movement of the sliding shaft 14 and the tool element carrier 12 in an advancing position in which the sliding shaft 14 is slid in the distal direction in relation to the basic position discussed above, in which the sliding shaft 14 is slid to a maximum extent in the proximal direction relative to the tool element carrier 12.

The locking device 168 defines a release position in which the sliding shaft 14 and the tool element carrier 12 can be displaced in parallel to the longitudinal axis 148 or in parallel to the sliding direction 16. Further, the locking device 168 defines a locking position in which a movement of the sliding shaft 14 relative to the tool element carrier 12 is blocked in at least the proximal direction.

The locking device 168 comprises a first locking element 170 and a second locking element 172.

The locking elements 170 and 172 in the locking position interengage with one another in a force-locking and/or positive-locking manner. In the release position, they are out of engagement.

The second locking element 172 is arranged or formed on the sliding shaft 14. The first locking element 170 is transferable from the release position into the locking position by a movement in the direction toward the sliding shaft 14.

The second locking element 172 and the sliding shaft 14 are formed in one piece, namely monolithically. In the embodiment of the sliding shaft instrument 10 depicted in FIGS. 1 to 10, the second locking element 172 is configured in the form of a retaining groove 174 that is open facing away from the sliding shaft 14. Said retaining groove 174 annularly surrounds the sliding shaft 14 and is self-enclosed. The retaining groove 174 is thus configured in the form of an annular groove.

The second locking element 172 comprises a stop face 176 that faces in the proximal direction. The stop face 176 forms a side wall of the retaining groove 174.

The stop face 176 is somewhat inclined facing in the direction toward the sliding shaft 14. An angle of inclination 178 between the stop face 176 and the sliding direction 16 is in a range of about 88° to about 60°.

The stop face 176 together with an annular face 180 of the retaining groove 174 facing away from the longitudinal axis 148 in the radial direction defines an undercut 182, which is formed on the second locking element 172.

The first locking element 170 is arranged on the sliding shaft instrument 10 in such a way that it is arranged or formed so as to be immovable or substantially immovable relative to the tool element carrier 12 in the sliding direction 16. This is achieved by the first locking element being arranged or formed on the coupling portion 84, held so as to be immovable relative to the tool element carrier 12 in the working position in the axial direction, i.e., in parallel to the sliding direction 16.

The first locking element 170 comprises a lever arm 184, which extends pointing in the distal direction in parallel to the sliding direction 16. The lever arm 184 is fixed to the sliding shaft instrument 10 on the proximal side, namely by it being formed in one piece with the coupling portion 64.

The first locking element 170 further comprises a locking projection 186, which points in the direction toward the sliding shaft 14 and in the release position is out of engagement with the second locking element 172. The release position is depicted as an example in FIG. 7. In the locking position, the locking projection 186, as is schematically depicted in FIG. 9, is in engagement with the second locking element 172.

The locking device 168 further comprises a restoring device 188. The restoring device 188 is arranged and configured in such a way that the first locking element 170 is movable against the action of the restoring device 188 from the release position into the locking position.

The restoring device 188 comprises a restoring element 190, which is arranged or formed so as to cooperate with the first locking element 170.

In the embodiment of the sliding shaft instrument 10 depicted in FIGS. 1 to 10, the restoring element 190 is configured in the form of a spring element 192, namely in the form of a leaf spring 194. The lever arm 184 also comprises or forms the restoring element 190.

As is schematically depicted in FIG. 9, by exerting a pressing force, symbolized by the arrow 196, on a free end of the lever arm 184, the first locking element 170 can be pivoted against the action of the restoring element 190 with the locking projection 186 in the direction toward the longitudinal axis 148.

The first locking element 170 further comprises a latching nose 198. The latching nose 198 in the locking position engages in a positive-locking or substantially positive-locking manner into the undercut 182 on the second locking element 172, as is schematically depicted in FIG. 9. The latching nose 198 is arranged or formed pointing in the distal direction, namely on the locking projection 186 in the embodiment depicted in the Figures. Said locking projection 186 is arranged or formed on a free end of the lever arm 184 as described.

The sliding shaft instrument 10 further comprises a securing device 200 for securing the locking device 168 in the locking position.

The securing device 200 comprises the first locking element 170 and the second locking element 172, which are arranged or formed in such a way that the locking device 168 can only be released by a movement of the sliding shaft 14 in the distal direction. This is achieved in the embodiment of the sliding shaft instrument 10 depicted in FIGS. 1 to 10 by the securing device 200 comprising the undercut 182 and the latching nose 198.

When the undercut 182 and the latching nose 198 are in engagement, the sliding shaft instrument 10 is secured in the locking position.

To release the locking position, the sliding shaft 14 must be slid somewhat in the distal direction. This is achieved by the actuating elements 50 and 52 being pivoted somewhat toward one another, thereby sliding the driving member 84 with the sliding shaft 14 coupled thereto in the coupling portion 64 somewhat in the distal direction. The latching nose 198 and the undercut 182 thereby come out of engagement and the restoring element 190 moves the locking projection 186 out of the retaining groove 174. The sliding shaft instrument 10 now adopts the release position. The sliding shaft 14 can be slid relative to the tool element carrier 12 within the range of the predetermined displacement path 130 in the sliding direction 16 in the distal and proximal direction.

To transfer the sliding shaft instrument 10 from the release position into the locking position, first the sliding shaft 14 must be slid so far in the distal direction that the locking projection 186 can dip with the latching nose 198 into the retaining groove 174. The engagement of the locking projection 186 is effected by exerting a pressing force on the free end of the lever arm 184.

If the actuating elements 50 and 52, with the locking projection 186 pushed forward, are not pressed further together, the biasing device 62, by exerting a biasing force acting in the proximal direction on the actuating elements 50 and 52, moves the coupling portion 64, which is movably coupled to the actuating device 18, somewhat in the proximal direction, namely so far until the latching nose 198 engages into the undercut 182. The sliding shaft instrument 10 in an advancing position of the sliding shaft 14, which is defined between the extreme positions in the proximal and distal direction, is now blocked and secured against a movement of the sliding shaft 14 in the proximal direction relative to the tool element carrier 12.

In the embodiment of the sliding shaft instrument 10 depicted in FIGS. 1 to 10, the described first locking element 170 is configured in the form of a pawl 102 that engages directly on the sliding shaft 14 in the locking position.

The sliding shaft instrument 10 described in the context of FIGS. 1 to 10 can be used, as already explained, to hold and handle a clip 30 in a partially open position, in particular to be passed to a surgeon by a person assisting said surgeon.

The basic structure of the sliding shaft instrument 10 can be maintained in further embodiments. Variants of the locking device 168 of the sliding shaft instrument 10 are explained in more detail in the following in connection with FIGS. 11 to 14.

The embodiment of the locking device 168, as it is schematically depicted in FIG. 11, comprises two first locking elements 170. They are arranged opposite one another on the coupling portion 64, so that to block a movement of the sliding shaft 14 relative to the tool element carrier 12 in the proximal direction only one of the two locking projections 168 has to be inserted into the retaining groove 174. Configuring the locking device 168 with two first locking elements 170 enables, in particular, a more flexible handling of the sliding shaft instrument 10.

In the embodiment that is depicted in FIG. 12, instead of a retaining groove the second locking element 172 is configured in the form of a retaining projection 204 pointing away from the sliding shaft 14 in the radial direction. The retaining projection 204 also surrounds the sliding shaft 14 annularly and is self-enclosed. The retaining projection 204 is thus configured in the form of an annular projection.

The annular projection has a stop face 176 that faces in the proximal direction and in turn is inclined in relation to the sliding direction 16 or the longitudinal axis 148 and defines an angle of inclination 178. An undercut 182 is thus formed in turn, into which a latching nose 198 on the latching projection 184 can engage in the locking position.

Depicted schematically with dashed lines in FIG. 12 is a second locking element 170, such that here, too, as in the embodiment of the locking device 168 depicted in FIG. 11, one of the two first locking elements 170 can selectively be brought into engagement with the retaining projection 204 in order to prevent a movement of the sliding shaft 14 relative to the tool element carrier 12 in the proximal direction.

In the embodiment of the locking device 168 depicted in FIG. 12, no corresponding surface facing counter to the stop face 176 is associated which could block a movement of the sliding shaft 14 in the distal direction, as is possible in the case of the retaining grooves 174 of the embodiments of FIGS. 1 to 10 and 11.

A further embodiment of a locking device 168 is schematically depicted in FIG. 13. It differs in its structure from the embodiment of FIGS. 1 to 10 through the design of the first locking element 170. The second locking element 172 in turn is configured in the form of a retaining groove 174, which comprises a stop face 176 that faces in the proximal direction and defines with the annular surface 180 an undercut 182.

The first locking element 170 comprises a bolt-shaped locking element portion 206 extending transversely to the sliding direction 16, on the end of which facing away from the sliding shaft 14 an actuating button 208 is arranged. Arranged on the end of the locking element portion 206 pointing away from the actuating button 208 and in the direction toward the sliding shaft 14 is a locking projection 186 with a latching nose 198 pointing in the distal direction for being brought into force-locking and/or positive-locking engagement with the undercut 182.

Arranged on the sleeve 66 is a hood 210, which has a perforation 212 for the locking element portion 206.

Arranged on the locking element portion 206 somewhat at a distance from the actuating button 208 is a stop plate 216, a restoring element 190 in the form of a coil spring 214 being supported on the side face, facing in the direction toward the sliding shaft 14, of said stop plate 216, on the one hand, and on the sleeve 66, on the other hand, and holding the first locking element 170 in the release position.

When an actuating force is exerted on the actuating button 208 in the direction toward the sliding shaft 14, the locking element portion 206, which is surrounded in sections by the retaining element 190, is moved against the action of said retaining element 190 toward the sliding shaft 14.

When the sliding shaft 14 is moved so far in the distal direction that the locking projection 186 can dip into the retaining groove 174, the sliding shaft 14 and thus sliding shaft instrument 10 can be blocked in the advancing position in the described manner.

A further embodiment of a locking device 168 is schematically depicted in FIG. 14. In this embodiment, too, the second locking element 172 is again configured as a retaining groove 174 with an undercut 182 acting in the proximal direction.

The first locking element 170 is similar in its structure and its functionality to the first locking element 170 described in the context of FIGS. 1 to 10.

Arranged on the sleeve 66 of the coupling portion 64 is a bearing block 218 projecting in the radial direction from the longitudinal axis 148, on which bearing block 218 a rigid, i.e., substantially non-deformable, lever arm 184 extending in the distal direction is mounted so as to be pivotable about a pivot axis 220. The lever arm, in turn, bears on its end pointing in the distal direction a locking projection 186, which is configured projecting from the lever arm 184 in the direction toward sliding shaft 14. A latching nose 198, in turn, projects in the distal direction from the latching pro- jection 186, which latching nose 198 together with the undercut 182 forms a securing device 200 described in detail above.

The pivot axis 220 extends transversely to the sliding direction 16.

The restoring device 188 comprises a restoring element 190 in the form of a coil spring 214, which is supported on the sleeve 66 on the one hand and on the lever arm 184 on the other hand. This makes it possible to pivot the lever arm 184 by applying a pressing force in the direction toward the sliding shaft 14, namely against the action of the restoring element 190.

As already explained several times above, the locking projection 186 can dip into the retaining groove 174 when the sliding shaft 14 is moved sufficiently far in the distal direction out of its basic position.

When the securing device 200 is released by moving the sliding shaft 14 in the distal direction, the restoring element 190 moves the lever arm 184 back into its initial position in which the locking projection 186 and the retaining groove 174 are out of engagement. The sliding shaft 14 can now be moved in the distal and proximal direction within the predetermined displacement path 130.

The described locking devices 168 can, as explained, be combined with the described basic structure of the sliding shaft instrument 10 as desired. Thus, different embodiments of sliding shaft instruments 10 in the form of clip appliers 222 can be configured.

The described embodiments of locking devices 168 have a significantly longer lifespan, can be produced more easily, are simpler to handle, and offer an increased reliability compared to conventionally known locking devices that are made of thin sheet metal. This is of great interest in particular in the case of the use of the medical sliding shaft instrument 10 in neurosurgery in order to, in particular, prevent an unintentional release of a clip 30 held with the sliding shaft instrument 10 in the head of a patient.

The invention claimed is:

1. A medical sliding shaft instrument comprising a tool element carrier, a tubular sliding shaft surrounding the tool element carrier and defining a sliding direction, and an actuating device for moving the sliding shaft relative to the tool element carrier in a distal direction, wherein at least one tool element is arranged or movably mounted on a distal end of the tool element carrier, wherein the at least one tool element is arranged or formed so as to cooperate with a distal end region of the sliding shaft in such a way that the at least one tool element is moved as a result of movement of the sliding shaft in the distal direction, wherein the sliding shaft instrument further comprises a locking device for blocking movement of the sliding shaft relative to the tool element carrier in at least one advancing position, wherein the sliding shaft in the at least one advancing position is displaced in the distal direction in relation to a basic position in which the sliding shaft is displaced to a maximum extent in a proximal direction relative to the tool element carrier, wherein the locking device defines a release position in which the sliding shaft is displaceable relative to the tool element carrier, and a locking position in which movement of the sliding shaft relative to the tool element carrier in at least one of the proximal and the distal direction is blocked, wherein the locking device comprises at least one first locking element and at least one second locking element, which in the locking position are in at least one of force- locking and positive-locking engagement and in the release position are out of engagement, wherein the at least one second locking element is arranged or formed on the sliding shaft and wherein the at least one first locking element is transferable from the release position into the locking posi- tion by movement toward the sliding shaft, and wherein the at least one first locking element is connected to the tool element carrier by a resilient spring that biases the at least one first locking element from the locking position to the release position, in such a way that the at least one first locking element is movable by overcoming a resilient biasing force generated by the resilient spring to move the at least one first locking element from the release position into the locking position.

2. The medical sliding shaft instrument according to claim 1, wherein the at least one second locking element and the sliding shaft are formed in one piece.

3. The medical sliding shaft instrument according to claim 1, wherein the at least one first locking element is at least one of:

a) movable in a direction transverse to the sliding direc- tion from the release position into the locking position; and b) arranged or formed on the sliding shaft instrument so as to be immovable or substantially immovable relative to the tool element carrier in the sliding direction.

4. The medical sliding shaft instrument according to claim 1, wherein the actuating device comprises two actuating elements that are movable relative to one another.

5. The medical sliding shaft instrument according to claim 4, wherein the actuating device comprises a coupling part, wherein the two actuating elements are movably arranged on the coupling part, and wherein the tool element carrier is immovably held on the coupling part in a working position.

6. The medical sliding shaft instrument according to claim 1, wherein the sliding shaft instrument comprises a biasing device for exerting a biasing force acting in the proximal direction on the sliding shaft.

7. The medical sliding shaft instrument according to claim 1, wherein the at least one second locking element comprises a stop face facing in the proximal direction.

8. The medical sliding shaft instrument according to claim 7, wherein the at least one second locking element has an undercut and wherein the undercut is delimited at least partially by the stop face.

9. The medical sliding shaft instrument according to claim 8, wherein the at least one first locking element comprises a latching nose, which in the locking position engages in a positive-locking or substantially positive-locking manner into the undercut on the at least one second locking element.

10. The medical sliding shaft instrument according to claim 7, wherein the stop face is inclined facing in a direction toward the sliding shaft.

11. The medical sliding shaft instrument according to claim 1, wherein the at least one second locking element is at least one of:

a) configured as a retaining projection pointing in a radial direction from the sliding shaft or configured as a retaining groove that is open facing away from the sliding shaft; and b) arranged such that the at least one second locking element annularly surrounds the sliding shaft.

12. The medical sliding shaft instrument according to claim 1, wherein the at least one first locking element comprises a locking projection pointing in a direction toward the sliding shaft, where the locking projection in the locking position is in engagement with the at least one second locking element.

13. The medical sliding shaft instrument according to claim 1, wherein the at least one first locking element comprises a locking element portion extending transversely to the sliding direction.

14. The medical sliding shaft instrument according to claim 1, wherein the sliding shaft instrument comprises a securing device for securing the locking device in the locking position.

15. The medical sliding shaft instrument according to claim 1, wherein the sliding shaft instrument comprises a stop device for delimiting movement of the sliding shaft in the proximal direction and in the distal direction.

16. The medical sliding shaft instrument according to claim 1, wherein the tool element carrier is coupled to the actuating device in a working position and is separated from the actuating device in a cleaning position.

17. The medical sliding shaft instrument according to claim 1, wherein at least one of:

a) the at least one first locking element is configured as a pawl that engages on the sliding shaft in the locking position;

b) the sliding direction runs rectilinearly or in a curved manner;

c) the at least one tool element and the tool element carrier are formed in one piece; and d) the sliding shaft instrument is configured as a clip applier.

18. A medical sliding shaft instrument comprising a tool element carrier, a tubular sliding shaft surrounding the tool element carrier and defining a sliding direction, and an actuating device for moving the sliding shaft relative to the tool element carrier in a distal direction, wherein at least one tool element is arranged or movably mounted on a distal end of the tool element carrier, wherein the at least one tool element is arranged or formed so as to cooperate with a distal end region of the sliding shaft in such a way that the at least one tool element is moved as a result of movement of the sliding shaft in the distal direction, wherein the sliding shaft instrument further comprises a locking device for blocking movement of the sliding shaft relative to the tool element carrier in at least one advancing position, wherein the sliding shaft in the at least one advancing position is displaced in the distal direction in relation to a basic position in which the sliding shaft is displaced to a maximum extent in a proximal direction relative to the tool element carrier, wherein the locking device defines a release position in which the sliding shaft is displaceable relative to the tool element carrier, and a locking position in which movement of the sliding shaft relative to the tool element carrier in at least one of the proximal and the distal direction is blocked, wherein the locking device comprises at least one first locking element and at least one second locking element, which in the locking position are in at least one of force-locking and positive-locking engagement and in the release position are out of engagement, wherein the at least one second locking element is arranged or formed on the sliding shaft and wherein the at least one first locking element is transferable from the release position into the locking position by movement toward the sliding shaft, wherein the at least one second locking element comprises an annular stop face facing in the proximal direction, wherein the stop face extends radially relative to the sliding direction and also in the proximal direction, from an outer wall of the sliding shaft to a radially-outward end of the stop face, to define an undercut extending in the distal direction between the outer wall and the radially-outward end of the stop face, and wherein the annular stop face extends entirely around the sliding shaft.

19. A medical sliding shaft instrument comprising a tool element carrier, a tubular sliding shaft surrounding the tool element carrier and defining a sliding direction, and an actuating device for moving the sliding shaft relative to the tool element carrier in a distal direction, wherein at least one tool element is arranged or movably mounted on a distal end of the tool element carrier, wherein the at least one tool element is arranged or formed so as to cooperate with a distal end region of the sliding shaft in such a way that the at least one tool element is moved as a result of movement of the sliding shaft in the distal direction, wherein the sliding shaft instrument further comprises a locking device for blocking movement of the sliding shaft relative to the tool element carrier in at least one advancing position, wherein the sliding shaft in the at least one advancing position is displaced in the distal direction in relation to a basic position in which the sliding shaft is displaced to a maximum extent in a proximal direction relative to the tool element carrier, wherein the locking device defines a release position in which the sliding shaft is displaceable relative to the tool element carrier, and a locking position in which movement of the sliding shaft relative to the tool element carrier in at least one of the proximal and the distal direction is blocked, wherein the locking device comprises at least one first locking element and at least one second locking element, which in the locking position are in at least one of force-locking and positive-locking engagement and in the release position are out of engagement, wherein the at least one second locking element is arranged or formed on the sliding shaft and wherein the at least one first locking element is transferable from the release position into the locking position by movement toward the sliding shaft, and wherein the at least one second locking element comprises an annular stop face that extends radially relative to the sliding direction from an outer wall of the sliding shaft to a radially-outward end of the stop face, and wherein the annular stop face extends entirely around the sliding shaft.

20. The medical sliding shaft instrument according to claim 19, wherein the at least one second locking element is formed as an annular groove on the sliding shaft, wherein the annular groove is open in a radial direction with respect to the sliding direction.

* * * * *